US010370776B2

(12) United States Patent
Longo et al.

(10) Patent No.: US 10,370,776 B2
(45) Date of Patent: Aug. 6, 2019

(54) ANTIBODY LIKE PROTEIN

(71) Applicants: Michael Longo, Whittier, CA (US); Rajika Perera, Cambridge (GB)

(72) Inventors: Michael Longo, Whittier, CA (US); Rajika Perera, Cambridge (GB)

(73) Assignee: IDEA ORCHARD, LLC, City of Industry, CA (US)

( * ) Notice: Subject to any disclaimer, the term of this patent is extended or adjusted under 35 U.S.C. 154(b) by 773 days.

(21) Appl. No.: 14/497,320

(22) Filed: Sep. 25, 2014

(65) Prior Publication Data

US 2016/0090400 A1 Mar. 31, 2016
US 2016/0222065 A9 Aug. 4, 2016

Related U.S. Application Data

(60) Provisional application No. 61/882,572, filed on Sep. 25, 2013.

(51) Int. Cl.

*C40B 40/10* (2006.01)
*C40B 10/00* (2006.01)
*C40B 40/08* (2006.01)
*C12N 15/10* (2006.01)

(52) U.S. Cl.

CPC ............ *C40B 40/10* (2013.01); *C12N 15/102* (2013.01); *C12N 15/1031* (2013.01); *C12N 15/1037* (2013.01); *C40B 10/00* (2013.01); *C40B 40/08* (2013.01); *C07K 2319/20* (2013.01); *C07K 2319/50* (2013.01); *C07K 2319/70* (2013.01);

(Continued)

(58) Field of Classification Search

CPC ........... C07K 2319/20; C07K 2319/50; C07K 2319/70; C12N 15/102; C12N 15/1031; C12N 15/1034; C12N 15/1037; C12N 15/1058; C40B 10/00; C40B 40/08; C40B 40/10

See application file for complete search history.

(56) References Cited

U.S. PATENT DOCUMENTS 9,493,523 B2 11/2016 Kojoh et al.
2013/0225434 A1* 8/2013 Kay ...................... G01N 33/68 506/9

FOREIGN PATENT DOCUMENTS

WO WO 2014/152660 A1 9/2014

OTHER PUBLICATIONS

Osuna et al. (Nucleic Acids Research, 2004, 32(17):e136).*

(Continued)

*Primary Examiner* — Jeremy C Flinders
(74) *Attorney, Agent, or Firm* — Kleinberg & Lerner, LLP; Marvin H. Kleinberg

(57) ABSTRACT

A general method and recombinant nucleic acid sequences, by means which the method selects a recombinant protein containing an FHA domain for binding a target molecule from a library proteins with a high-throughput method of creating protein variations within the FHA domain in non-conserved or non-structural sequences of the FHA scaffold, and the library may also be in the form of a phagemid or phage library wherein the ALP nucleic acid sequence is inserted into a vector capable of allowing the vector and expressed ALP protein from being virally packaged, and the recombinant nucleic acid sequences which are randomly mutated at varying non-conserved or non-structural FHA domain sequences.

22 Claims, 4 Drawing Sheets

Specification includes a Sequence Listing.

(52) U.S. Cl.
CPC ...... *C12N 15/1034* (2013.01); *C12N 15/1058* (2013.01)

(56) References Cited

OTHER PUBLICATIONS

Pershad PhD Thesis (Year: 2012).*

Kritika Pershad, et al. "Directed Evolution of the Forkhead-Associated Domain to Generate Anti-Phosphospecific Reagents by Phage Display," Journal of Molecular Biology, Nov. 23, 2012, pp. 88-103, vol. 424, issues 1-2.

Yu-Ming M. Huang, et al. "Achieving Peptide Binding Specificity and Promiscuity by Loops: Cases of the Forkhead-Associated Domain," PLoS One, May 28, 2014, pp. e98291, vol. 9, issue 5.

Christian Tiede, et al. "Adhiron: a stable and versatile peptide display scaffold for molecular recognition applications," Protein Engineering Design and Selection, Advance Access published Mar. 25, 2014, May 1, 2014, pp. 145-155, vol. 27, issue 5.

Michaela Gebauer, et al. "Engineered protein scaffolds as next-generation antibody therapeutics," Current Opinion in Chemical Biology, Jun. 2009, pp. 245-255, vol. 13, issue 3.

Robbie Woodman, et al. "Design and Validation of a Neutral Protein Scaffold for the Presentation of Peptide Aptamers," Journal of Molecular Biology, Oct. 7, 2005, pp. 1118-1133, vol. 352, issue 5.

* cited by examiner

```
                          I                              II                                III
KIF1C 528  ...VDMDIKLTGQFIREQHCLFRSIPQPDGEVVVTLEPCEGAETYVNGKLVTEPLVLKSGNRIVMGKNHVFRFNH...  599
1R21   33  ...IECDIRIQLPVVSKQHCKIEIHEQ---EAILFHNFSSTNPTQVNGSVIDEPVRLKHGDVITI-IDRSFRYEN...  100
```

Figure 2.

```
aaaaaaccat gggcactccc cacctggtga acctgaacga agaccctctg atgtctgagt    60

gtctgctcta ccacatcaaa gatggcgtca ccagggtcgg ccaagtagat atggacatca   120

                I
agctgaccgg acagttcatt cgggagcaac actgtctgtt ccggagcatc ccccagccag   180

                                   II
atggagaagt ggtggtcact ctggagcctt gtgaaggagc tgagacatat gtgaatggga   240

                                                           III
agcttgtgac ggagccgctg gtgctgaagt cagggaatag gattgtgatg ggcaagaacc   300

acgttttccg cttcaaccac gcggccgcaa aaaa                               334
```

Figure 3.

ANTIBODY LIKE PROTEIN

BACKGROUND OF THE INVENTION

1. Field of the Invention

The present invention relates to a recombinant protein molecule, and namely a recombinant protein with modifiable binding properties to a variety of target molecules, and the recombinant protein may comprise of an antibody-like scaffold moiety wherein amino acid sequences within the scaffold are specifically or randomly altered, and random alteration of said amino acid sequences may generate a library of variant proteins where one or more proteins are capable to specifically bind to one or more target molecules, and selected variants of the recombinant protein with binding specific properties may be used as a reagent, a diagnostic or therapeutic agent.

2. General Background and State of the Art

The efficacy of a protein purification method relies on specificity of the target protein as well as efficiency both in cost and in time. The need for efficient protein purification is essential for the scientific understanding and societal applications of proteins in everyday life.

Antibodies bind in a highly specific manner to their antigen. Thus, producing an antibody which binds to a particular protein of interest is a highly sought after goal which has a wide range of applications. However, antibodies require much expense and time to produce as the production of antibodies often require immunization of animals with prepared antigens of a protein against the antigen and then isolation of the antigen specific binding antibodies. The process is costly and time consuming, and not tightly controlled as to the nature and purity of the antibody. Production of purified monoclonal antibodies, which may reduce possible artifacts in protein isolation or analysis, is far more costly and time consuming than standard polyclonal antibody production.

Recombinant antibodies can be developed from screenable libraries (e.g., phage display libraries), however, the expression of such recombinant antibodies in standard expression systems such as *E. coli* is problematic as yields tend to be suboptimal. As a result, alternative antibody-like scaffolds which retain the capacity to bind specifically to a target but can be highly expressed in *E. coli* is desirable.

The display of antibodies as antigen-binding fragments (Fabs) and single-chain variable fragments (scFvs) on filamentous phage was first described in 1990 (McCafferty et al. Nat. 348:552-54 (1990)). It provides a powerful technique for selecting a specific antibody from a mixed population of antibodies together with the gene that codes for it. The ability to co-select proteins and their genes has been exploited to enable the isolation of antigen-specific antibodies directly from repertoires or "libraries" of rearranged V-genes derived from unimmunized humans.

This ability to isolate human antibodies that bind to human proteins is of major importance for the creation of therapeutics. The problem with using murine monoclonal antibodies as therapeutics has been that they are frequently recognized as foreign by the patient's immune system. Humanizing murine antibodies can resolve the problem.

The broader the range of the library, the higher the probability of selecting a high affinity antibody to a given target. Large libraries (Vaughn et al.) are capable of generating large panels of diverse, high affinity sub-nanomolar antibodies to a given antigen. This makes it easier to obtain an antibody with the desired characteristics and is useful for both therapeutic antibodies and antibodies that will be used as research tools and reagents.

Antibodies are displayed on the surface of phage in the form of scFvs fused to the N terminus of the gIII protein. Phage with specific binding activities can then be isolated from antibody repertoires after repeated rounds of selection.

Recombinant antibodies have become an important and routinely used tool in scientific research and have also been implemented for uses in diagnostics of disease as well in various therapeutic approaches. Over 30% of biopharmaceuticals in development are recombinant antibodies of which a majority are applied towards therapies against tumor diseases and inflammation (Holliger P. et. al. Nat. Biotechnol. 23(9):1126-36 (2005), Adams G P. et. al. Nat. Biotechnol. 23(9):1147-57 (2005); Chang J T et. al. Nat. Clin. Pract. Gastro. Hepa. 4:220-8 (2006). The immunization of an animal with a specific antigen allows for the production and purification of polyclonal antibodies which can be used as detection and diagnostic reagents. However, such animal produced antibodies are limited in their use due to batch-dependence and are restricted in therapeutic application due to their immunogenicity within humans.

The generation of monoclonal antibodies through the invention of hybridoma technology helped circumvent the problems associated with polyclonal antibodies where the specificity of a particular antibody could be directed towards a desired target. The production of humanized monoclonal antibodies involves the fusion of myeloma cell lines with human B cells or transgenic murine B cells carrying a repertoire of human IgG (Lonberg N. Nat. Biotechnol. 23(9):1117(2005); Fishwild D M. et. al. Nat. Biotechnol. 14(7):845-51 (1996); Jakobovits A. Curr. Opin. Biotechnol. 695):561-6 (1995)). However, the production of monoclonal immunoglobulins from hybridomas is still dependent on in vivo methods of immunization which requires donors as well as a successful immune response. Techniques such as phage display and ribosomal display solve many of the problems associated with generating polyclonal and monoclonal antibodies as well as provide a means of improving antibodies through genetically engineering humanized versions of antibodies or fragments thereof (Hoogenbroom H R. Nat. Biotechnol. 9:1105-16 (2005); Hust M. et. al. Mol. Biol. 295:71-96 (2005)).

Unfortunately, the complex structure of antibodies poses challenges in their production. Antibodies are large protein structures that contain two light chain LC and two heavy chain HC polypeptides which are interlinked with each other in an intricate manner by numerous disulfide bridges and non-covalent interactions (Elgert K. Immunolog: Understanding the Immune System, Chapter 4:Antibody Structure and Function (1998)). Such a multifaceted protein structure requires an oxidizing environment and appropriate intracellular chaperones to assist in obtaining proper folding. Hence, cells of eukaryotic origin provide superior intracellular conditions and the protein infrastructure necessary to assist in the correct folding of antibodies.

Mammalian cells are used in the production of 60-70% of all known approved recombinant protein pharmaceuticals (Schirrmann et. al. Front. Biosci. 13:4576-94 (2008)). The advantage of using a mammalian cell line in the production of antibodies is their ability to mediate advanced protein folding and post-translational modifications. However, immunoglobulin production using mammalian cell lines is expensive. Furthermore, they raise the risk of contamination with viral pathogens or prion diseases such as bovine spongiform encephalopathy through the frequent use of undefined bovine serum in growth media. Alternatively, insect cells such as High Five or Schneider 2 cell lines are capable of complex protein folding and consequently may be used for the production of recombinant antibodies. Their disadvantage however, lies in their high cost of production, long duration before obtaining a protein product, as well as observable differences in protein glycosylation patterns (Hsu et. al. J. Biol. Chem. 272(14):9062-70 (1997)).

Yeast are an attractive alternative for the production of recombinant immunoglobulins due to their advantages of quick time of expansion, inexpensive growth conditions, can be readily altered through genetic engineering, and their capability to post-translationally modify and secrete proteins (Kim H. et. al. FEMS Yeast Res. (2014)). On the other hand, yeast may prematurely terminate transcription thus failing to express AT-rich genes (Ramanos M. et. al. Yeast 8:423-488 (1992)). Also, the propensity of yeast to hyperglycosylate heterologous proteins is problematic to producing a non-immunogenic therapeutic recombinant antibody (Sethurman N. et. al. Curr. Opin. Biotechnol. 17:341-346 (2006)).

Bacteria such as *E. coli* is the most common organism used for over-expressing and producing recombinant proteins. Ease and affordability of growth, rapid production of large quantities of protein, and ease of genetic manipulation make *E. coli* an attractive selection for the production of therapeutic recombinant immunoglobulins. Though the expression and modification of a full length immunoglobulin in a bacterial host strain is highly inefficient, smaller antibody fragments that maintain antigenic binding specificity can be readily produced in *E. coli* (Fellhouse F A. et. al. Making and Using Antibodies Ch. 8 CRC Press (2006)). Among the polypeptides that can be displayed on the surface of a phage library are antibodies and antibody fragments such as Fab and $scF_V$s as described by McCafferty et. al. Nat. 348(6301):552-554 (1990); Barbas et. al. Proc. Natl. Acad. Sci. 88(18):7978-82 (1991); Burton et. al. Proc. Natl. Acad. Sci. 88(22): 10134-7 (1991); Barbas et. al. Proc. Natl. Acad. Sci. 89(10):4457-61 (1992); and Gao et. al. Proc. Natl. Acad. Sci. 96(11): 6025-30 (1999). Combining the in vitro selectivity process of a phage or ribosomal display with the production of small recombinant proteins makes *E. coli* a prime source for the expression of antibody like fragments. Furthermore, using synthetic DNA to introduce diversity into the antigen binding site within the antibody like proteins described herein circumvents the requirement of a natural donor.

Protein phosphorylation is an important post-translational modification that is vital for the proper function of a wide variety of proteins. Typically, a serine, threonine, or tyrosine residue within a protein may be phosphorylated which in turn may mediate a conformational change and influence the regulation of a protein's function (Johnson L N. Biochem. Soc. Trans. 37(4)627-41 (2009)). The recognition of said phosphorylated residues is also critical in relaying signaling events downstream of the effector protein. Protein domains such as Src homology-2 (SH2) and phosphotyrosine binding domains (PTB) recognize phosphotyrosine residues, whereas phosphoserine and phosphothreonine may be recognized by the 14-3-3 family of proteins, proteins that contain a tryptophan-tryptophan (WW) domain, and by the forkhead associated (FHA) domain which predominantly recognizes phosphothreonine epitopes with less specificity towards phosphoserine and phosphotyrosine (Yaffe M B Structure 7; 9(3):R33-8 (2001)).

The FHA domain is associated with proteins that are involved in diverse functions such as signal transduction cascades, gene expression and transcription, protein translocation, DNA repair, and protein degradation (Durocher D. et. al. FEBS 513:58-66 (2001)). For example, the FHA1 domain of yeast protein kinase Rad53 is involved in phospho-dependent protein:protein interactions with phosphorylated Rad9 following DNA damage and repair signaling (Durocher D. et. al. Mol. Cell 4:387-94 (1999); Lee S J. Mol. Cell Biol. 23(17):6300-14 (2003)). FHA domain containing members of the UNC104 kinesin family of proteins such as KIF1A, KIF1B, and KIF1C as well as in the KIF14 family of proteins in humans are involved in vesicular transport (Bloom G S. Curr. Opin. Cell Biol. 13:36-40 (2001); Hall D H. et. al. Cell 65:837-847 (1991); Yonekawa Y. et. al. J. cell Biol. 141:431-441 (1998); Zhao C. et. al. Cell 105:587-597 (2001)). Furthermore, FHA-containing transcription factors such as Fkh1 and Fkh2 have been identified in *S. cerevisiae*. Fkh1 and Fkh2 have both been shown to be master regulators of G2 transcription during yeast budding and associate with Sir2 as a means of transcription control under oxidative stress (Durocher D. et. al. FEBS 513:58-66 (2001); Linke C. et. a. Front Physiol. 4:173 (2013)).

FHA domains span approximately 100-140 amino acids in length and contain two directionally opposing β-sheets, each with five and six β strands, which fold into a β-sandwich structure that are interconnected by α-helical loops (Yaff M B. Structure 9:R33-38 (2001); Huang Y M. PlosOne 9:5 (2014)). Changes in the loop regions are the principal distinction that mediates FHA domain specificity to various target proteins (Huang Y M. PlosOne 9:5 (2014)). There are over 100 structures of FHA domains deposited in the Protein Data Bank. Protein sequence alignments of FHA domains reveal that there is a low sequence identity within the FHA family domain, however, there are five key conserved amino acid residues within the loop regions that are considered to be involved in phosphopeptide recognition (Durocher D. et. al. Mol. Cell 6:1169-82 (2000)). Although the sequences within the loop regions vary, the principle arrangement of the loop regions coordinates phosphate group binding (Huang Y M. PlosOne 9:5 (2014)).

There is currently no molecule that can support the equivalent specificity in antibody based purification and characterization techniques that is less expensive and with less delay. Furthermore, there is no molecule that is more tightly controlled for obtaining highly specific and consistent protein isolation or characterization results.

INVENTION SUMMARY

The invention is a recombinant protein that contains antibody like scaffolding wherein sequences embedded in the protein are replaced with a variety of sequences capable of supporting specific binding to a variety of target proteins for isolation or characterization. Such recombinant proteins can also be used as therapeutic molecules by specifically targeting proteins and interfering with specific protein-protein and/or protein-nucleic acid interactions. The antibody like protein (herein "ALP") contains the forkhead-associated ("FHA") domain which is naturally known to recognize phosphothreonine epitopes on proteins. However, in this present invention, the FHA loop domains ("loop domains") portions, which are not essential for its protein structure, may be modified such that it is capable of supporting a wide range of antigen binding. The variety of modified FHA domains may then be used to generate a vast library capable of high throughput screening of antigen binding.

The ALP would be constructed from an insertion of its gene sequence into a cloning vector. Sequences that fall within the loops that emerge from the scaffold for which a specific sequence is not necessary to support the scaffold's structure, or in the sequences that are non-highly conserved and fall within or adjacent to said loop regions would be replaced with a variety of sequences that were selected based on a random set of amino acids or constructed through the use of software algorithms. Each variation of the ALP will be expressed and the variety of modified ALP will provide a library capable of high throughput screening for antigen specific binding.

The ALP may be attached to a resin wherein the resin is capable of being used in any protein isolation methods. The ALP may be tagged or fused to another protein. The ALP may be used in any library screening technique for isolating novel ALP interactions. The ALP may be used in any protein characterization methods once specific binding to protein has been established for any one or more variations of the ALP. The ALP may be used in Western blots. The ALP may be used with magnetic beads. The ALP may be fused to fluorescent markers or incorporate radioisotopes. The ALP may be used to specifically target a protein in vivo, interfering with that protein's function or neutralizing its deleterious effects. The ALP may be used in methods requiring protein binding as part of a therapeutic application.

The novel features which are characteristic of the invention, both as to structure and method of operation thereof, together with further objects and advantages thereof, will be understood from the following description, considered in connection with the accompanying drawings, in which the preferred embodiment of the invention is illustrated by way of example. It is to be expressly understood, however, that the drawings are for the purpose of illustration and description only, and they are not intended as a definition of the limits of the invention.

DESCRIPTION OF THE DRAWINGS

FIG. 2. Sequence alignment of a portion of the FHA domain in KIF1C with a portion of the FHA domain from PDB file 1R21 identifying the variable loops I, II, and III denoted in the boxed regions FIG. 3. A segment of the amplified KIF1C nucleotide sequence as obtained using PCR primers SEQ ID1 and SEQ ID2. Nucleotide sequences representing at least three of the variable loops are underlined and indicated as I, II, and III.

DETAILED DESCRIPTION OF THE INVENTION

(i) Definitions

Figure 1:
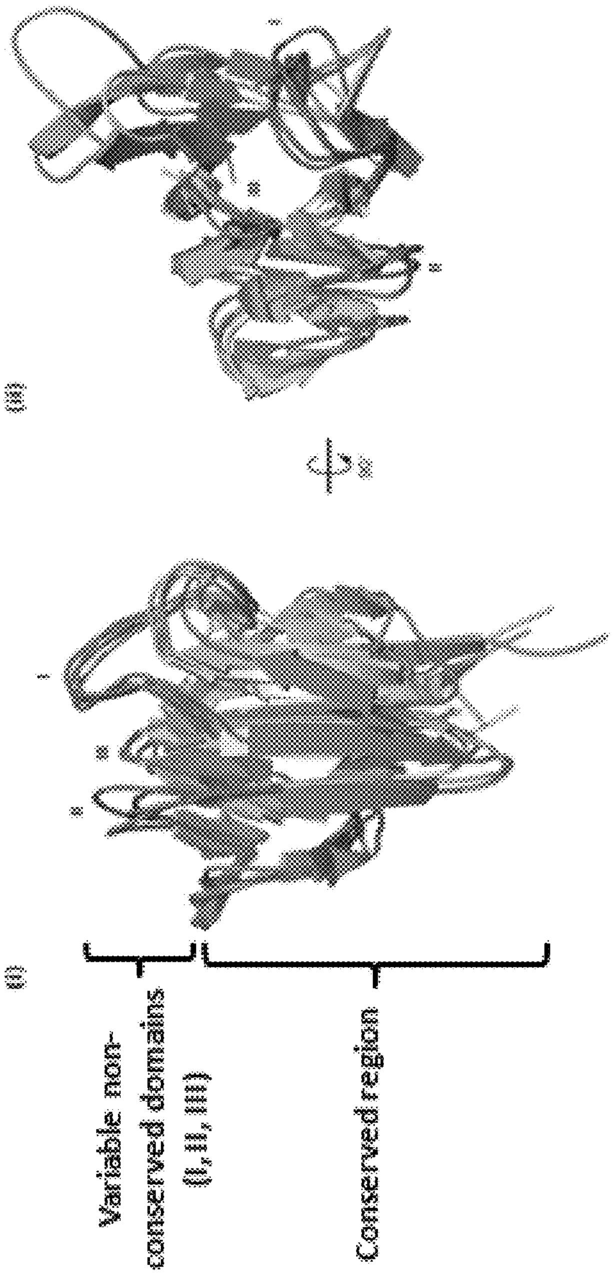
FIG. 1. Superimposition of PDB files 1R21, 3POA, 3MDB, and 3KT9. Loops containing variable sequences are indicated as I, II, and III.

The following definitions, unless otherwise stated, apply to all aspects and embodiments of the present application.

The present invention contemplates the production of a recombinant protein nucleic acid.

An "oligonucleotide" refers to a single stranded DNA, RNA, or a DNA-RNA hybrid nucleic acid strand that may be approximately 18 to 30 nucleotides in length. Oligonucleotides can hybridize to genetic material such as DNA, cDNA, or mRNA. Oligonucleotides can be labeled at their 5'-terminus via an amino- or thiol-linker or at the 3'-terminus via an amino link with, but not limited to, fluorophores such as Cy3™, Cy5™, fluorescein, quenchers such as Dabcyl or T-Dabsyl, or alternative labels such as biotin and radioisotopes. Labeled oligonucleotides may function as probes to detect the presence of nucleic acids with a complementary nucleic acid sequence. Labeled or unlabeled oligonucleotides may also be used as primers necessary for performing PCR when cloning or detecting the presence of a gene. Oligonucleotides are prepared synthetically by solid-phase synthesis using modified or unmodified 2'-deoxynucleosides (dA, dC, dG, and dT) or ribonucleosides (A, C, G, U).

The terms "protein", "peptide", and "polypeptide" refer to a linear macromolecular polymer of at least two natural or non-natural amino acids covalently linked together by peptide bonds. A protein, peptide, or polypeptide has a free amino group at the N-terminus and a free carboxyl group at the C-terminus unless circular or specifically tagged at the N- or C-terminus. The amino acid sequence of a protein, peptide, or a polypeptide is determined by the nucleotide sequence of a gene. Proteins, peptides and polypeptides may have a primary, secondary, and tertiary structure. At times, the protein, peptide, or polypeptide may also be post-translationally modified with prosthetic groups or cofactors.

The term "gene" refers to a specific DNA sequence that can be transcribed into RNA which can then be translated into a peptide or a polypeptide. Regions in the DNA sequence of a gene may also include regulatory regions, the transcribed sequence for RNA, and the coding sequence with a start and stop codon that is translated into a protein. Transcriptional and translational regulatory regions that control the expression of a gene may include promoters, enhancers, terminators, and in the case of eukaryotic expression a polyadenylation signal.

The term "cloning vector" refers to pieces of nucleic acid that can be used for the insertion and stable preservation of foreign pieces of DNA within an organism. The cloning vector may be a plasmid, bacteriophage, cosmid, bacterial artificial chromosome, or a yeast artificial chromosome. Cloning vectors may be used for creating genomic libraries such as in the invention herein.

A "plasmid" is a vector that refers to an independently replicating circular double-stranded piece of DNA. The plasmid may contain an origin of replication such as the *E. coli* oriC, a selectable antibiotic resistance gene conferring resistance to, but not limited to, β-lactam, macrolide, and aminoglycosides antibiotics, a promoter sequence under expression control, and a multiple cloning site containing restriction sites which may or may not contain a coding sequence for an antibody like protein described herein.

The plasmid may be an "expression plasmid". Expression plasmids allow for the expression of a cloned gene. An expression plasmid contains an inducible promoter region that allows for the regulation and induction of gene expression of a gene cloned into the plasmid's multiple cloning site, a ribosomal binding site, a start codon, a stop codon, and a termination of transcription sequence.

The term "promoter sequence" is a region of DNA either upstream or downstream from the site of initiation of transcription of a gene. As used herein, a bacterial promoter includes necessary consensus sequences of TTGACA at the −35 and a Pribnow box TATAAT sequence at the −10 position upstream of the start of transcription, and may also contain an UP element upstream of the −35 region.

The term "bacteriophage" refers to a broad group of over 5000 viruses in at least 13 virus families that infect bacteria as described by Moat et. al Microbial Phys. $4^{th}$ ed. Ch. 6 (2002). The genome "core" of a bacteriophage may be either double or single stranded, linear or circular, DNA or RNA and is surrounded by coat of proteins termed the "capsid". A single infectious bacteriophage unit is referred to as a "virion". Phage such as M13, fd, and f1, as described herein, attach to the sex F-pili carried on an F-plasmid in *E. coli* and are referred to as "male-specific phages". The M13, fd, and f1 are closely related filamentous phage and code for 11 proteins. Five of the proteins are involved in forming the capsid structure and six of the proteins are involved in viral replication and assembly. Gene VIII codes for a major coat protein, whereas genes III, VI, VII, and IX code for minor proteins found at the tip ends of the phage structure. The N-terminus of the geneIII protein product binds to the F-pilus in *E. coli* while the C-terminus remains anchored in the phage coat. The N-terminus of the geneIII protein product may be fused to $scF_V$ fragments as in a phage display described herein. McGrath et. al. Bacteriophage: Genetics and Molecular Biology Acad. Press. (2007).

The terms "phage display" and "phage library" refer to a defined and well known technique used for the display and production of polypeptides on the surface of a phage virus as first described by Smith G P. Sci. 228(4705):1315-7 (1985). Among the polypeptides that can be displayed on the surface of a phage library are antibodies and antibody fragments such as Fab and $scF_V$s as described by McCafferty et. al. Nat. 348(6301):552-554 (1990), Barbas et. al. Proc. Natl. Acad. Sci. 88(18):7978-82 (1991), Burton et. al. Proc. Natl. Acad. Sci. 88(22): 10134-7 (1991), Barbas et. al. Proc. Natl. Acad. Sci. 89(10):4457-61 (1992), and Gao et. al. Proc. Natl. Acad. Sci. 96(11): 6025-30 (1999). In a phage display, non-essential genes of a bacteriophage are removed and a unique gene of interest in the form of cDNA, herein the cDNA encoding for the antibody like protein, is inserted into the phage gene sequence encoding the phage surface protein of a phage display vector. Bacteria such as *E. coli* are transformed with the phage display vector as well as infected with a helper phage enabling for the expression and packaging of the relevant cDNA encoding a polypeptide product, such as the antibody like protein described herein, on the bacteriophage surface. A library of phage with the displayed antibody like proteins can then be screened and selected for by binding to a specific target or molecule of interest. One example of a target of interest is an antigen. Once a phage that exhibits binding to a target has been identified, the phage can then be isolated and used for a second round of infection and screening. Multiple rounds of screening and selection can be performed to identify the most optimal target binding polypeptide.

The term "ribosome display" refers to a technique that is used to identify and evolve a select protein that binds to a specific target. In a ribosome display, DNA from an oligonucleotide library is inserted and ligated into a ribosome display vector. The inserted gene of interest is then amplified via PCR. In vitro transcription transcribes the amplified PCR product into mRNA which is then translated in vitro. The mRNA-ribosome-polypeptide complex is then used for affinity assays by binding the complex to an immobilized target. Non-binding mRNA-ribosome-polypeptide complexes are removed by washing and the target bound mRNA-ribosome-polypeptide complex is recovered. The mRNA from the recovered mRNA-ribosome-polypeptide complex may be amplified by PCR and the display selection process may then be repeated to enrich for a gene product with enhanced target specificity. Random mutations may be introduced after each round of selection to further enrich for a gene product with enhanced target specificity.

The term "forkhead-associated domain" (FHA domain) refers to a modular phosphopeptide recognition domain that predominantly recognizes phosphothreonine, and to a lesser extent phosphoserine and phosphotyrosine, epitopes on proteins. The FHA domain may be present on a variety of proteins including kinases, phosphatases, kinesins, transcription factors, RNA-binding proteins, and metabolic enzymes and is involved in phospho-dependent protein: protein interactions such as signal transduction, transcription, protein transport, DNA repair, and protein degradation. The FHA domain may be approximately 100 to 140 amino acid residues in length and folded into a β-sandwich structure of directionally opposing β-sheets interconnected by α-helix loops.

The term "recombinant protein" refers to a protein that is expressed from an engineered "recombinant DNA" coding sequence. Recombinant DNA combines at least two separate DNA strands into one strand that would not have been normally made in nature. Molecular cloning is used to construct recombinant DNA and may involve the amplification of a DNA fragment of interest and then inserting the fragment into a cloning vector. The recombinant DNA is then introduced into a host organism which is then screened and selected for the presence of the inserted recombinant DNA.

The term "amplification" refers to the act of mass replication of a genetic sequence. Amplification of a genetic sequence may be performed by PCR using primers that hybridize to flanking ends of a genetic sequence of interest. Amplification of a genetic sequence may also be performed in vivo by transforming bacteria with a plasmid or transfecting a host cell with a virus that carries the recombinant genetic sequence of interest.

The term "protein expression" refers to the production of protein within a host cell such as a bacteria, yeast, plant, or animal cell. A vector carrying the coding sequence for a recombinant protein under the control of a promoter, such as an expression plasmid, is inserted into a host cell. The promoter controlling the expression of the recombinant gene is then induced and the protein encoded by the recombinant gene is produced within the host cell.

The term "protein purification" refers to a process of purifying a protein and may employ any technique used to separate and isolate a protein of interest to a satisfactory level of purity. Protein purification exploits a protein's various properties such as size, charge, binding affinity, and biological activity. Liquid column chromatography is commonly used in protein purification where a cell lysate containing an expressed protein is passed over a "resin" with particular binding affinity for the protein of interest. A resin is a compound or a polymer with chemical properties that supports the purification of proteins via ion exchange, hydrophobic interaction, size exclusion, reverse phase, or affinity tag chromatography. A protein may also be purified by non-chromatographic techniques such as through the electroporation of protein from an excised piece of a polyacrylamide gel that contained a protein sample of interest.

The term "MALDI" refers to matrix-assisted laser desorption ionization which is a mass spectrometry technique used to analyze compounds, and biomolecules such as polypeptides and proteins, by determining their molecular masses. A protein sample is first prepared for MALDI by enzymatic digestion with a protease such as trypsin. The sample is then chemically coupled to a matrix and then introduced into the mass spectrometer. A pulsed laser beam targets the sample which results in desorption and ionization of the polypeptide from a solid to a gas phase. The vaporized ions are accelerated in an electric field towards a detector. Peptide fragments are then identified based on their mass-to-charge ratio via peptide mass fingerprinting or tandem mass spectrometry. The peptide masses are displayed as a list of molecular weight peaks which are then compared to a database of known peptide masses such as that of Swis-sprot allowing for a statistical identification of the original protein sample.

A "protein tag" refers to an amino acid sequence within a recombinant protein that provides new characteristics to the recombinant protein that assist in protein purification, identification, or activity based on the tag's characteristics and affinity. A protein tag may provide a novel enzymatic property to the recombinant protein such as a biotin tag, or a tag may provide a means of protein identification such as with fluorescence tags encoding for green fluorescent protein or red fluorescent protein. Protein tags may be added onto the N- or C-terminus of a protein. A common protein tag used in protein purification is a poly-His tag where a series of approximately six histidine amino acid residues are added which enables the protein to bind to protein purification matrices chelated to metal ions such as nickel or cobalt. Other tags commonly used in protein purification include chitin binding protein, maltose binding protein, glutathione-S-transferase, and FLAG-tag. Tags such as "epitope tags" may also confer the protein to have an affinity towards an antibody. Common antibody epitope tags include the V5-tag, Myc-tag, and HA-tag.

The terms "fusion protein" or "fused protein" refer to a protein that is coded by a single gene and the single gene is made up of coding sequences that originally coded for at least two or more separate proteins. A fusion protein may retain the functional domains of the two or more separate proteins. Part of the coding sequence for a fusion protein may code for an epitope tag. As described herein for the antibody like protein, a fusion protein may also contain sequences that code for a variety of proteins having varying functional roles based on its application.

The term "protein coding sequence" refers to a portion of a gene that codes for a polypeptide. The coding sequence is located between an ATG initiation of translation codon and the location of a TAG, TAA, or TGA termination of translation codon. Typical to eukaryotic genes, the coding sequence may include the "exons" of a gene, which is the sequence of a gene that is transcribed and translated into a polypeptide and may exclude the "introns" of a gene, which is the sequence of a gene that is transcribed but not translated into a polypeptide.

The term "transformation" refers to a process of introducing exogenous genetic material into a bacterium by methods employing membrane permeability via chemical or electrical means. Performing a transformation involves adding genetic material, such as a plasmid, to an aliquot of competent bacterial cells, such as *E. coli*, and allowing the mixture to incubate on ice. The bacterial cells are then either electroporated or placed at 42° C. for approximately 1 minute and then returned to incubate on ice. The bacterial cells are then grown on an agar plate overnight until colonies are visible. The agar plate may contain antibiotic or nutrient conditions for colony selection.

The term "transfection" refers to the process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. "Transduction" is often used to describe virus-mediated DNA transfer. *Nature Methods* 2, 875-883 (2005).

The term "Western blot" refers to an analytical technique used to determine the presence of a polypeptide. A Western blot is performed by initially separating proteins on a sodium dodecyl sulfate polyacrylamide gel (SDS-PAGE), and then electro-transferring the separated proteins onto a filter membrane such as a nitrocellulose of PVDF membrane. The membrane is then incubated with a blocking buffer that may contain a blocking agent such as bovine serum albumin or non-fat dry milk. The membrane is then incubated with a primary antibody that is specific for the polypeptide of interest. The primary antibody is washed off from the membrane and the membrane is then incubated with a secondary antibody that is conjugated to a compound or an enzyme that allows for detection and visualization.

The term "homologous sequence" refers to an amino acid or nucleotide sequence that is at least 70% to 99% homologous to a corresponding reference sequence. Sequences that are 90% identical have no more than one different amino acid per 10 amino acids in the reference sequence. The percentage of homology between two or more sequences may be identified using a homology algorithm of Smith and Waterman (1970) Adv. Appl. Math2:482c, Needleman and Wunsch (1970) J. Mol. Biol. 48:433, or Pearson and Lipman (1988) Proc. Natl. Sci. 85:2444. The methods of sequence alignment are known to those in the art. A computer based program employing the mentioned or alternative sequence comparison algorithms may be used such as BLAST as described in The NCBI Handbook (2002) or ClustalOmega as described in Sievers et. al. Mol. Sys. Bio. 7:539 (2011).

The terms "antibody" and "immunoglobulin" are interchangeable and refer to a polypeptide tetramer macromolecule that recognizes and binds, with high affinity and precision, to a binding site referred to as an "epitope" on an antibody target molecule referred to as an "antigen". Antibodies are made up of two identical "heavy chains" and two identical "light chains" referring to the size of each of the individual polypeptide components of an antibody. Each chain is composed of a variable domain and a constant domain, such as the variable heavy and light chains, $V_H$ and $V_L$, respectively, and the constant heavy and light chains, $C_H$ and $C_L$, respectively. The heavy and light chains are interconnected with disulfide bonds to form a Y like structure. The antibody Y like structure can be separated into two regions: the top Fab region and the bottom Fc region. The Fab region contains the variable domains and is responsible for antigen recognition, whereas the Fc region is responsible for inducing effector functions and cellular responses. A review of antibody characteristics and antibody structure is provided in Antibodies: A Laboratory Manual, Second Edition, Cold Spring Harbor Laboratory Press (2013).

The term "scF$_V$" refers to a single chain $F_V$ antibody that consists of a heavy chain variable domain $V_H$ and a light chain variable domain $V_L$ that are joined together by a flexible linker to form a single polypeptide. The scFV antibody fragment can be presented on the surface of a bacteriophage as described herein in the antibody like protein phage library.

The pSANG4 phagemid display vector is a modified version of the parent pHEN1 phagemid vector initially described in U.S. Pat. No. 5,565,332A and in Hoogenboom et. al. Nuc. Aci. Res. 19:15 4133-4137 (1991). pSANG4 was constructed by inserting a novel cloning linker region into pHEN1. To construct pSANG4, the primers NcNotlinkS (GCCCAGCCGGCCATGGCCCAGGTGCAGCTG-CTC-GAGGGTGGAGGCGGTTCAGGCGGAGGTGGCTCT) and NcNotlinkA (TTTT-TGTTCTGCGGCCGCGT-CATCAGATCTGCCGCTAGCGCCACCGCCAGAGC-CAC CTCCGCCTGAACC) were annealed, amplified via PCR, and then cut with NcoI/NotI and then cloned between the NcoI/NotI sites of pHEN1 to generate pSANG3. Antibody light chains and heavy chains were then cloned between the NheI/NotI, and NcoI/XhoI sites, respectively. The pelB sequence was then replaced with a signal sequence from M13 gene III to create pSANG4. An M13 leader and 5' UTR were also cloned in between the HindIII and NcoI sites using the primers G3hind NdeS (TGATTACGC-CAAGCTTTTAGGAGCCTTTTTTTTTGGAGATTTTCA-ACCATATGAAAAAATTATTATTCGCAATT) and G3NcoA (CTGCACCTGGGCCAT-GGCCGGCTGGGC-CGCATAGAAAGGAACAACCAAAGGAATTGC-GAATAATAATT TTTTCA). The design of pSANG4 is described in detail in Schofield et. al. Gen. Bio. 8:R254 (2007).

The term "fluorescent label" refers to a "fluorophore" that may be covalently attached to a polypeptide or a nucleic acid. Fluorophores absorb light energy at a specific excitation wavelength and re-emit light energy at a specific lower emission wavelength as described by Lakowicz J R. in Principles of Fluorescence Spectroscopy $3^{rd}$ ed. Springer Publishing (2006). Fluorescent labels allow for the detection and localization of a labeled polypeptide or nucleic acid through the use of a microscope that detects fluorescence, a flow cytometer, or any other instrument capable of detecting fluorescence. The labeling, detection, and localization of fluorescently labeled proteins has been described in detail by Modesti M., Meth. in Mol. Bio. 783:101-20 (2011) and Giepmans et. al., Science 312:5771 (2006). Common fluorophores include but are not limited to Alexa Fluor®, Cy®3 and Cy®5, FITC, TRITC, DAPI, APC, R-PE, and Qdot® as provided by Life Technologies in their Fluorophore Selection guide (www.lifetechnologies.com) and Thermo Scientific (www.piercenet.com).

A "therapeutic molecule" refers to a chemical compound that provides a medicinal purpose. Therapeutic molecules may be any drug, anesthetic, vitamin or supplement known in the art, and may be listed in the Orange Book of Approved Drug Products with therapeutic Equivalence Evaluations provided by the U.S. Food and Drug Administration (www.accessdata.fda.gov) or any chemical, drug, or biological molecule listed in the Merck Index (www.rsc.org/merck-index).

The term "conserved sequence" refers to a sequence of nucleotides in DNA or RNA, or amino acids in a polypeptide, that are similar across a range of species. Conserved sequences are represented by a nucleotide or an amino acid that occurs at the highest frequency at a particular site in a homologous gene or protein from the same or different species. The term "non-conserved sequence" refers to a sequence of nucleotides or amino acids in a gene or protein that are not conserved and that have a higher variability than conserved sequences.

(ii) Sequences and Agents of the Application

The present invention provides for novel gene sequences encoding for a variety of ALPs wherein each ALP may contain substantially all conserved scaffolding sequences of the FHA domain, but vary in sequences that fall between the conserved scaffolding sequences. FIG. 1 shows a three-dimensional model of an FHA domain that may be used in an ALP with annotations that identify the conserved and less conserved sequences. The originating sequence may be obtained from the human Kinesin family member 1C (KIF 1C) at chromosomal location 17p13.2. (See Sequence ID 9) Additional alterations may be introduced in the conserved scaffolding sequences so long as substantially all the scaffold structure is retained. Such alterations may allow the FHA domain conserved regions to provide varying levels of affinity of ALP to various proteins.

At least one or more of the less or non-conserved regions of the gene encoding for ALP are typically found in the three less conserved loop domains of the FHA domain: loop I, II, and III, as shown in FIG. 1 and identified in the amino acid alignment sequence in FIG. 2. Other substitutions or alterations may be employed in other regions so long as the scaffolding structure is sufficiently maintained to allow for targeted binding. These regions may be mutated, partially or totally deleted, or replaced with a variety of sequences. In addition, post-translational modifications may be employed following ALP expression.

Modifications of the ALP's FHA loop domains may be accomplished via recombinant DNA methods such as restriction endonuclease based insertions and ligations or through methods not requiring endonucleases such as In-Fusion® HD cloning as described by Clontech Laboratories Inc. (www.clontech.com). In the alternative, site-directed mutagenesis may be used to incorporate mutations. A library of ALPs may be constructed using semi-random primers with site-directed mutagenesis. The ALP library may be expressed and the resultant proteins may be employed as part of a high throughput screen for protein/antigen specific binding. ALPs demonstrating specific binding may then be selected and utilized for both research and therapeutic purposes.

In an alternative embodiment, the less or non-conserved regions of ALP gene may be specifically altered to encode for an ALP that specifically recognizes a particular protein or class of proteins or other molecule. For example, the sequence may encode for a number of negatively charged amino acids which may selectively bind to DNA binding proteins. The insertion sequence may also encode for a known binding domain of another protein that specifically recognizes another molecule. In another embodiment, the loop portions may be engineered such that the ALP may specifically target an individual molecule or a metal ion (i.e. chelator).

In the exemplary embodiment, the FHA domain DNA sequence may be amplified by PCR using the human Kinesin family member 1C (KIF 1C). See SEQ ID NO. 9. Primer sequences used to amplify the FHA domain fragment from the KIF1C gene SEQ ID NO. 9 may be the forward primer SEQ ID NO. 1 and the reverse primer SEQ ID NO. 2 which may be used to generate the amplified FHA domain sequence. See SEQ ID NO. 10. Amplification may introduce an NcoI restriction endonuclease site by the forward primer and a NotI restriction endonuclease site by the reverse primer.

Other sources of the FHA domain that may be amplified using similar primers to the primers listed in Seq. 1 and Seq. 2 may be from any of the FHA domain containing sequences such as from the genes KIF1A and KIF1B coding kinesin like proteins present in humans or from the kinesin like protein UNC-104 in *Caenorhabditis elegans*, or KAPP from Aridopsis species, or Rad53, Fh1, Hcm1, Fkh1, Fkh2, Dunt, Spk1, and Mek1 from yeast species such as *Sacharomyces cerevisia* as described in Kim et. al. J. Bio. Chem. 277: 38781-90 (2002). Other sources of the FHA domain may be from the human CHFR or MKI67 genes Durocher et. al. FEBS 513:58-66 (2001). As known by a person of ordinary skill in the art, similar or newly synthesized primers may be constructed to amplify and isolate replicated copies of other DNA containing homologs of the FHA domain that are found in other genes from other sources.

The amplified sequence containing the FHA domain that forms the unmodified ALP may be inserted into a plasmid for recombinant cloning of the gene which the plasmid may also serve as an expression vector of ALP. Insertion into a plasmid may be carried out by first digesting both the parent plasmid and the PCR fragment with the appropriate restriction enzymes. The cut DNA are then purified and incubated with a ligase followed by purification.

The amplified sequence may also be inserted adjacent to another gene that encodes for another protein thereby creating a fusion protein. Following the insertion and cloning of the FHA gene containing sequence, modifications to FHA loop domain sequences as well as other possible variable sequences may be carried out to create ALPs for binding specific target molecules.

Possible bacteria that may be used for the cloning and expression of the recombinant vector may be D5α, BL21, BL21 (DE3), JM109, JM109 (DE3), HB101 or derivatives thereof. Possible plasmids for gene modification and protein expression in said bacteria may be any of the pET vectors as described in the Novagen pET System Manual (www.emdmillipore.com/) or any pBAD expression vectors provided by Invitorgen Life Technologies (www.lifetechnologies.com). In the alternative, the protein may be expressed in mammalian cells where insertions within the looped domain may require post-translational modifications. Possible plasmids for use in mammalian cellular expression systems may be a pcDNA expression vector under the control of a CMV promoter such as pcDNA3.1+ as provided by Life Technologies (www.lifetechnologies.com) or a high expression vector such pEF-BOS or a pEF-BOS derivative as described by Mizushima et. al. Nuc. Adi. Res. 18:17 (1990).

In an exemplary embodiment, the amplified FHA domain sequence may be inserted into unique NcoI and NotI sites of the pSANG4 (Schofield D J. et. al. Gen. Bio. 8:R254 (2007)). The primers SEQ ID NO. 1 and SEQ ID NO. 2 that amplify this sequence from the KIF1C gene contain NcoI and NotI sites which provide complimentary overhangs that enable a directional insertion of the ALP sequence into the pSANG4 vector. Expression of ALP is controlled by a lac promoter located upstream of the NcoI site.

Further to the present invention, the ALP gene may be inserted adjacent to other sequences encoded for other protein or protein domains. Such protein sequences may encode for marker proteins such as but not limited to GFP, transcription factors, signal peptides for protein transport, or phage display proteins such as the geneIII protein. Other sequences may encode for tags such as, but not limited to, a MYC tag, His tag, FLAG tag, Strep tag, MBP tag, GST tag or any other protein tags known in the art.

Intervening sequences between ALP and adjacent proteins may contain linker sequences and may be used where the encoded sequence may contain a peptide sequence that is devoid of any steric hindrance on the ALP or other adjacent proteins. Intervening sequences may also contain residues easily recognized and accessed by proteases. Intervening sequences may also contain other sequences functional at the nucleotide level such as stop codons, promoters of ALP, antisense sequences, bacterial Rho recognition sequences, or ribozyme encoding sequences. Such sequences may be used to regulate expression and gene stability.

In the exemplary insertion of ALP into the NcoI and NotI sites of the pSANG4 phagemid, expression is controlled by a lac promoter present upstream. Downstream of the ALP sequence is the PIII encoding sequence. When expressed, the fusion protein, ALP-PIII, is produced. A linker sequence also intervenes between the two protein encoding sequences and contains a trypsin digest site, a MYC tag, and an Amber stop codon. Upstream of the ALP encoding sequence is an M13 leader encoding sequence so as to direct the export of the fusion protein to the periplasm. It is understood by those with the ordinary skill in the art that other embodiments may contain tags and leader sequences and the recombinant ALP construction is not limited to a fused PIII.

Proteins may fold in a two-state kinetics manner where the N- and C-terminal ends are in close proximity or in direct contact with each other. In contrast, proteins that fold by non-two-state kinetics do not have their N- and C-terminals in contact and may be referred to as N-C no-contact proteins. It has been previously reported that approximately 50% of all known protein structures in the Protein Data Bank are two-state folded proteins where the N- and C-terminals of the protein structure have at least one contact in between them and 37% of those have at least two terminal residues in contact, Krishna M. et. al. PNAS (2005). The high frequency of proteins with N- and C-terminal contacts may be a characteristic of proteins that mediate protein stability. For example, N- and C-terminal contacts have been shown to play a critical role in protein stability of the GH10 family of xylanses in *Bacillus* sp. under condition of high temperature, alkali pH, proteases, and SDS treatment, Bhardwaj A. 5:6 (2010). Similarly, the stability of the human and mouse apolipoproteins A-I has been attributed to intermolecular interactions between the N- and C-terminal domains as demonstrated by Koyama A. et. al. Biochem. 48(11): 2529-37 (2009). Thus, maintaining or implementing N- to C-terminal interactions in recombinant proteins may be a strategy to confer stability of a recombinant protein structure as discussed in Bhardwaj et. al. Comp. Struc. Biotech. 2:3 (2012). Such protein engineering practices are employed in domain insertion and gene fusion technology as described by Doi N. et. al. FEBS 457:1-4 (1999) where the success of protein fusion is seemingly in part dependent on N- and C-terminal proximity, Ostermeier M. Pro. Eng. Des. Selec. 18:8 (2005).

In another embodiment of ALP, multiple FHA domains may be constructed wherein the protein may have one or more FHA domains. Because the N- and C-termini are in close proximity of each other, at least two FHA domains may be fused. Multiple FHA domains linked together may then bind a target molecule with its collective loops. The loop domains may be engineered for a specific target or a general class of target molecules. An ALP with multiple FHA domains may target a specific molecule or a polymeric macromolecule with a repeating structure. One embodiment may be an ALP with multiple FHA domains wherein the loop domains have a plurality of positive charges and are capable of binding a molecule displaying a plurality of negative charges.

Figure 4:
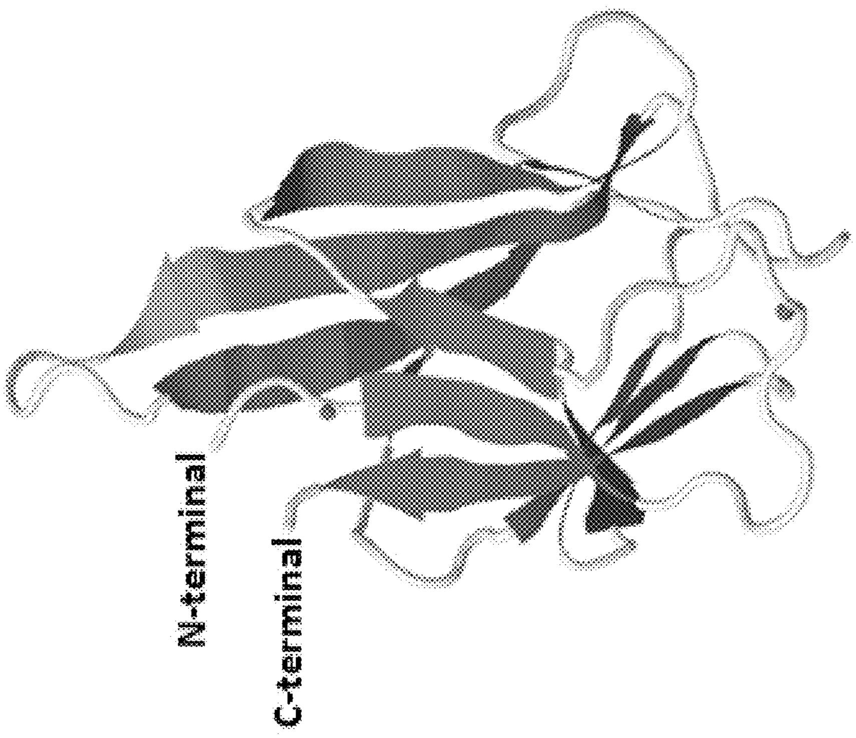
FIG. 4. Cartoon representation of the crystal structure of the human KIF1C protein (PDB file 2G1L). The N- and C-terminal domains are labeled and shown to be in close proximity to one another.

Further to the embodiment of the ALP that contains multiple FHA domains, the linker sequences between the FHA domain may encode for a protein that allows for free rotation of the domains or restricts movement of the FHA domains such that the loop domains are held in a specific orientation. This embodiment is possible given that the N- and C-termini are located in the native structure of the FHA domain in close proximity with each other which allows a linker sequence to be engineered between repeating FHA domains, see FIG. 4. Such an orientation may provide for stable target molecule recognition and binding. In the case of a target DNA sequence, tandem FHAs could be engineered to recognize palindromic sequences and require linker sequence that would hold the domains in a specific orientation so as to account for the three-dimensional orientation of the palindrome on the helix, similar to the lac repressor type construction.

ALPs may be separately expressed, but may form multimeric proteins in their native conformation. In one embodiment, the ALP may also contain the CC1 domain such that individual FHA domains may form homodimers. See Huo et al., Cell Struc., 20, 1550-1561, (2012).

In an exemplary embodiment, expression of the fusion protein ALP-PIII from a pSANG4 vector for the purposes of phage display may be based on a method described by Schofield et. al., Gen. Bio., 8, (R254)1-18 (2007). The ALP-PIII plasmid may be transformed in bacterial cells through electroporation or other equivalent methods. Bacterial cells expressing the F pilus were used for phage to gain entry into the cell. Possible cell lines which typically carry the low copy number F plasmid are preferred and may be, but are not limited to, the K12 derivative, TG1. After successful transformation and selection of colonies, expression of ALP-PIII is carried out under the absence of glucose. In cell lines that have the inducible RNA polymerase gene under the control of the lac promoter, IPTG may be used to induce expression for the ALP-PIII variants.

Further to this exemplary embodiment, the transformed bacterial cells may then be subjected to superinfection in order to produce recombinant phage particles. Helper phage such as M13KO7 or KM13 result in preferential packaging of the phagemid DNA into a phage particle, which displays the ALP-PIII protein.

An ALP affinity to a particular target molecule may be determined through the use of the engineered ALP's fused tag or monitoring of the target molecule directly to the ALP using either a solid phase or liquid phase method. The ALP protein in question would first be over expressed and isolated either by the fused tag or through some other equivalent means. The binding affinity may then be evaluated based on direct binding to the target molecule that may be affixed to solid or liquid phase support or through co-elution methods. In an exemplary co-elution method embodiment, an ALP with modified FHA loop domains and a fused His tag may be applied to an IMAC column. Binding may then be monitored via western blot analysis on elute fractions from the IMAC column via antibody detection of both the ALP and the target molecule.

Alternatively, ALP binding to the target molecule can be determined directly by fixing the antigen to a resin. In the exemplary embodiment of the phagemid ALP pSANG4, there is no His tag present in the encoded protein which allows the target molecule to contain a His tag. This is an effective method in binding antigens to an immobilized metal affinity resin either attached to a solid phase support or a liquid phase support (e.g. magnetic beads) followed by evaluating ALP binding and selecting for ALP binding.

ALP phage libraries may be constructed through the sub-cloning of modified ALPs inserted into a phagemid using semi-randomized primers targeting the FHA loop domains. In the exemplary embodiment, primers SEQ ID NO. 3, SEQ ID NO. 4, SEQ ID NO. 5, SEQ ID NO. 6, SEQ ID NO. 7, and SEQ ID NO. 8 may be used on parent ALP containing pSANG4 which generates more than a $10^{10}$ phage library. The ALP phage library may then be selected for binding to a target molecule that is immobilized on a solid or liquid phase resin. Bound ALP phages will then be eluted and subjected to further analysis and application. One preferred method is a solid phase selection ("panning") where a specific target molecule (i.e. antigen) is coated to the surface of a tube or microtiter plate well. After excess antigen is removed and remaining exposed surface is blocked using skimmed milk, the phage antibody library is applied and unbound phages are washed off. The remaining phage may be eluted by a variety of techniques such as low pH buffer (citrate) or high pH buffer (triethylamine) or alternatively, if a trypsin sensitive site was incorporated between the ALP and PIII, trypsin depending cleavage elution. Several rounds of panning may be required.

In the antibody like protein described herein, sequence variability may be introduced within the KIF1C FHA loop regions responsible for recognizing a phosphothreonine epitope. The said FHA domain loop regions are represented in an overlapped image of four independent three-dimensional structures of FHA domain containing proteins (1R21, 3KT9, 3MDB, and 3POA) deposited in the Protein Data Bank, FIG. 1 (http://www.rcsb.org). A protein sequence alignment of 1R21 and KIF1C identifying three loop regions in KIF1C is shown in FIG. 2. The genetic sequence coding for the three loop regions in KIF1C is shown in FIG. 3. The DNA nucleotide sequence of the KIF1C FHA domain that was cloned into a pSANG4 vector between a NcoI and NotI restriction sites is SEQ ID NO. 10. Variability of amino acid sequences within the KIF1C FHA domain loop regions may be introduced through mutagenesis using any of the primers listed in SEQ ID NO. 3 to 8 where an "a" refers to an adenine, a "g" refers a guanine, a "c" refers to a cytosine, a "t" refers a thymine, a "k" refers to a keto nucleotide which may be either a guanine or a thymine, and an "n" refers to any nucleotide.

The 5' and 3' ends of each of the said primers have a complementary sequence to KIF1C with a sequence of variable nucleotides corresponding to the coding sequence of the KIF1C loop regions in between the said complementary sequences. The variable nucleotide sequence in each of the said primers is designed to alter the nucleotide sequence of one or more of the FHA loop domains and nucleotides adjacent to the FHA loop domains. Primer SEQ ID NO. 3 may have 12 variable nucleotides located approximately within loop III and may be flanked by 18 and 24 nucleotides that are complementary to the KIF1C nucleotide sequence. Primer SEQ ID NO. 4 may have 15 variable nucleotides located approximately within loop II and may be flanked by 24 and 24 nucleotides that are complementary to the KIF1C nucleotide sequence. Primer SEQ ID NO. 5 may have 24 variable nucleotides located approximately within loop I and may be flanked by 24 and 24 nucleotides that are complementary to the KIF1C nucleotide sequence. Primer SEQ ID NO. 6 may have 33 variable nucleotides located upstream of loop I and may be flanked by 24 and 18 nucleotides that are complementary to the KIF1C nucleotide sequence. Primer SEQ ID NO. 7 may have 18 variable nucleotides located approximately between loop II and loop III and may be flanked by 24 and 24 nucleotides that are complementary to the KIF1C nucleotide sequence. Primer SEQ ID NO. 8 may have two variable nucleotide regions of 18 and 15 nucleotides that may be separated by 12 nucleotides complementary to the KIF1C nucleotide sequence and the first variable nucleotide region may be located approximately within loop II and the second variable nucleotide region may be located between loop II and loop III and the two variable nucleotide sequences may be flanked by 24 and 25 nucleotides that are complementary to the KIF1C nucleotide sequence. The cloned FHA domain of SEQ ID NO. 10 may be altered by any of the said primers and similar primers. Any of the nucleotides in the KIF1C FHA domain loop regions or nucleotides adjacent to or near the FHA domain loop regions may be mutated by any known mutagenesis technique known in the art.

Alternative methods of target molecule binding may use liquid phase selection. In one exemplary embodiment, an antigen may be attached to a magnetic bead (e.g. Dynal Talon Beads) via an affixed tag such as His tag wherein the magnetic beads contain a Ni-Chelate. Such a method may be preferred over a solid phase selection because the concentration of the antigen is more easily controlled as well as avoiding denaturation of certain antigens or ALP variants.

When multiple rounds of selection are used, the first round of selection may be purified with such methods such as PEG precipitation and CsCl gradient purification. Subsequent rounds of selection may be stored in an appropriate solution containing 50-10% glyercol at 20° C. to −80° C., respectively. The selected phage may then be transduced into fresh *E. Coli* and superinfected with helper phage for subsequent amplification.

Helper phage such as KM13 may be used wherein the PIII has been altered such that it is protease cleavable. (Kristensen and Winter 1998, Folding & Design 3.) A trypsin sensitive site was inserted between domains D2 and D3 on PIII. This exemplary helper phage may then be eliminated from selection by subjecting the rescued helper phage and ALP phages to a trypsin digest. The trypsin digest cleaves the PIII on the KM13 helper phage and thereby improves ALP phage selection. Digestion with trypsin also specifically elutes phages with a functional ALP moiety which have bound specifically to the antigen immobilized on a resin via the presence of a trypsin sensitive site in the linker sequence that is between the two residues.

In an exemplary embodiment for antigen binding, purity and activity of a protein antigen are crucial. Antigen preparations should avoid the presence of carrier proteins such as bovine serum albumin, and Tris or glycine based buffers which said buffers inhibit covalent coupling of antigen to biotin when applying soluble or "biotin selections" or the covalent coupling of antigen to derivatized surfaces. Quality control of the antigen may be done using gel electrophoresis or mass spectrosocpy. For therapeutic use, the biological activity of the antigen is also important, which in such cases a liquid phase selection may be employed.

The present invention provides for a novel set of protein sequences of the ALP protein. In the exemplary embodiment, a monomer ALP is fused with PIII and randomized peptides at FHA loop domain residues. Further to this exemplary embodiment are sequences of the M13 leader peptide, and the linker sequence between ALP and PIII which includes a MYC tag.

The ALP containing construct may also be expressed in a mammalian cell system using transient transfections. Possible cell lines may be HEK293E suspension cells. Expression vectors may be similar to those used in Schofield et al. (2007) which may be used to produce post translationally modified ALPs. Some examples may be adding a carboxy-terminal His10 tag or His10-rat Cdy (domains 3 and 4) fusion. The resultant protein may be purified using an FPLC system or Qiagen8000 robot or any other equivalent means that are known by one with an ordinary skill in the art.

(iii) Uses

The present invention may be used to construct ALP proteins which have modified FHA loop domain regions that specifically target other molecules. The ALP may be used in reagent, diagnostic, and therapeutic applications.

In an exemplary embodiment of phagemid using ALP-PIII fusion protein, a phage library may be constructed for obtaining ALP variants that selectively target a molecule or antigen. ALP variants that are positive for target molecule or antigen binding may then be used for research or diagnostic purposes. Selected ALP variants may be used to isolate target molecules as both an analytical and preparative method.

For one possible use, a selected ALP variant may be cleaved and affixed to a resin through a fused tag or an equivalent support phase and a research sample containing the target molecule may be extracted. Such use may be employed in, but is not limited to, chromatography, micro-titer plates, Western blots, ELISA, or magnetic bead based isolation.

Alternatively, a selected ALP may be used functionally to the action of target molecules. The target molecule may have an activity, and ALP binding may inhibit such activity. For example, a selected ALP may bind to an enzyme such that it prevents substrate binding. In the alternative, a selected ALP may bind to a signaling molecule which prevents the molecule from activating or act as a substrate for a particular biochemical pathway.

Similar to antibodies selected from phage library as discussed in Brekke & Sandie, Nature Reviews Drug Discovery 2, 52-62 (2003), selected ALP from a phage library may have three different therapeutic uses: by blocking the action of specific molecules, by targeting specific cells or by functioning as signaling molecules. The blocking activity of therapeutic ALP is achieved by preventing growth factors, cytokines or other soluble mediators from reaching their target receptors, which can be accomplished either by the ALP binding to the factor itself or ALP binding to its receptor.

Targeting specific cells involves directing ALP towards specific populations of cells. Selected ALPs can be engineered to carry effector moieties, such as enzymes, toxins, radionucleotides, cytokines or even DNA molecules, to the target cells, where the attached moiety can then exert its effect (for example, toxins or radionucleotides that can eliminate target cancer cells). Selected ALPs genes may be fused with antibodies wherein ALP binding may also allow binding to Fc receptors or binding to complement proteins and inducing complement-dependent cytotoxicity (CDC).

Alternatively, selected ALPs may be cloned into a recombinant virus and fused with viral protein factors. Because the N- and C-termini are close in proximity, that enables the selected ALP to be easily fused with another protein. In this present embodiment, the ALP gene may be inserted within the coding sequence of viral capsid protein, and thus the ALP fused protein would be displayed on the viral capsid. The viral capsid may contain therapeutic genetic material that is to be delivered to diseased cells. The viral capsid, such as in the case of the Adeno Associate virus, may be devoid of genetic material and instead contain drug molecules for treatment. ALP directed drug delivery may significantly increase the efficacy of pharmaceutical treatment by providing specific treatment while reducing collateral toxicity.

The signaling effect of ALPs depends on inducing cross-linking of receptors that are, in turn, connected to mediators of cell division or programmed cell death, or directing them towards specific receptors to act as agonists for the activation of specific cell populations. Another approach is to use ALPs as delivery vehicles for DNA or other molecules such as antigens to certain immune cells that present processed antigenic peptides, or epitopes, to T cells, to activate a specific immune response against that antigen.

Because ALPs may be easily fused with other proteins based on their close proximity of the N- and C-termini, fusion of ALPs with other proteins are not limited to the exemplary applications provided above. Fused proteins to the ALP may range from polypeptides that can serve as direct or indirect labels, recognizable protein tags, enzymes, transcription factors or structural proteins.

ALPs may also be fused to resins or supports for purification methods. ALPs may be attached to DNA molecules. ALPs may be linked to other molecules such as lipids that aid in drug delivery when the ALP is used therapeutically.

While the specification describes particular embodiments of the present invention, those of ordinary skill in the art can devise variations of the present invention without departing from the inventive concept.

What is claimed is:

1. A protein having an FHA domain comprising:

a. a scaffold domain and loop domains derived from a wild-type FHA domain;

b. at least one mutated loop domain;

c. at least one mutated scaffold sequence between the loops in regions that are non-highly conserved among wild-type FHA domains; and d. the protein having specific binding affinity to a target molecule that does not include interactions with phosphate moieties based on naturally occurring, or in vivo FHA domain recognition sites.

2. The protein of claim 1 wherein the mutations include post-translational modifications to the amino acid residues.

3. The protein of claim 1 wherein the mutations include a deletion, a replacement, or an addition to the amino acid residues.

4. The protein of claim 1 may be used for preparative, analytical, or therapeutic methods that involve the binding of said protein to said target molecule.

5. An isolated nucleic acid sequence encoding for said protein of claim 1.

6. The isolated nucleic acid sequence of claim 5 that encodes said protein is transfected into a host cell.

7. The isolated nucleic acid sequence of claim 5 wherein the expression of the isolated nucleic acid sequence allows the selected variant protein to be expressed from a host cell and bind to said target molecule.

8. The isolated nucleic acid sequence of claim 5 is combined with a second nucleic acid sequence that encodes for a second protein having specific binding affinity to a second target molecule, and that expression of the combined nucleic acid sequences creates an oligomeric protein capable of binding to multi-target molecules at the same time.

9. The protein of claim 1 further comprising at least one functional domain, linker sequence, sterically restricted intervening sequence, signal peptide, protease recognition site, and/or tag fused to the FHA domain.

10. The protein of claim 9 wherein the functional domain is an additional FHA domain.

11. The protein of claim 1 wherein the FHA domain is located within another functional domain.

12. The protein of claim 1 wherein the specific binding affinity activates, inhibits, or enhances a biochemical pathway.

13. The protein of claim 1, wherein the FHA domain is derived from SEQ ID No. 9.

14. An artificial protein capable of recognizing an epitope wherein the artificial protein comprising:

a. An FHA domain derived from SEQ ID NO. 9 having a scaffold domain and loop domains; and b. At least one mutated loop region or non-highly conserved sequence of the FHA domain, c. The protein having specific binding affinity to a target molecule that does not include interactions with phosphate moieties based on naturally occurring, or in vivo FHA domain recognition sites.

15. The protein of claim 14 further comprising at least one functional domain, linker sequence, sterically restricted intervening sequence, signal peptide, protease recognition site, and/or tag fused to the FHA domain.

16. The protein of claim 15 wherein the functional domain is an additional FHA domain.

17. The protein of claim 14 wherein the FHA domain is located within another functional domain.

18. The protein of claim 14 wherein the specific binding affinity activates, inhibits, or enhances a biochemical pathway.

19. The protein of claim 1 further comprising a multimer domain capable of forming multimeric proteins with at least one other protein molecule.

20. The protein of claim 19 wherein the multimer domain comprises a CC1 domain.

21. The protein of claim 14 further comprising a multimer domain capable of forming multimeric proteins with at least one other protein molecule.

22. The protein of claim 21 wherein the multimer domain comprises a CC1 domain.

* * * * *

SEQUENCE LISTING

```
<160> NUMBER OF SEQ ID NOS: 11

<210> SEQ ID NO 1
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 1

aaaaaaccat gggcactccc cacctggtga acctgaac                              38


<210> SEQ ID NO 2
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 2

tttttgcgg ccgcgtggtt gaagcggaaa acgtggtcc                              39


<210> SEQ ID NO 3
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 3

gtggttgaag cggaaaacnn knnknnknnk catcacaatc ctattccctg actt             54


<210> SEQ ID NO 4
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
```

-continued

<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 4
cacaagcttc ccattcacat atgtnnknnk nnknnknnka ggctccagag tgaccaccac     60

<210> SEQ ID NO 5
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 5
ggggatgctc cggaacagac agtgnnknnk nnknnknnkn nknnknnkca gcttgatgtc     60

<210> SEQ ID NO 6
<211> LENGTH: 75
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:

<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 6
gacgccatct ttgatgtggt agagnnknnk nnknnknnkn nknnknnknn knnknnkgtt     60
caccaggtgg ggagt                                                      75

<210> SEQ ID NO 7
<211> LENGTH: 66
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 7
aatcctattc cctgacttca gcacnnknnk nnknnknnkn nkcttcccat tcacatatgt     60
ctcagc                                                                66

-continued

<210> SEQ ID NO 8
<211> LENGTH: 99
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t

<400> SEQUENCE: 8
aatcctattc cctgacttca gcacnnknnk nnknnknnkn nkcttcccat tcacatatgt 60
nnknnknnkn nknnkaggct ccagagtgac caccacttc 99

<210> SEQ ID NO 9
<211> LENGTH: 4082
<212> TYPE: DNA
<213> ORGANISM: Homo sapiens

<400> SEQUENCE: 9
ctggggagta ggatggggct ccccctacga gggccggtgg cagccagaac tgatacagcc 60
cccctggtct ggggccagga cgccagctga ggagggcagg agtgtctgga gctatggctg 120
gtgcctcggt gaaagtggca gtgagggttc ggccctttaa cgcccgtgag accagccagg 180
atgccaagtg tgtggtcagc atgcagggca acaccacctc catcatcaat cctaaacaga 240
gcaaggatgc ccccaaaagc ttcacctttg actactccta ctggtcacac acttcgacgg 300 aggacccccca gtttgcatct cagcagcaag tgtatcggga cattggagaa gagatgctgc 360

-continued

```
tccacgcctt tgaaggctac aacgtgtgca tctttgccta tgggcagacc ggggctggga    420
aatcctatac catgatgggg cgacaggagc cagggcagca gggcatcgtg ccccagctct    480
gtgaggacct cttctctcgc gttagtgaga accagagtgc tcagctatcc tactctgtgg    540
aggtgagcta tatggagatc tactgtgagc gggtacgaga cctcttgaac cccaagagtc    600
ggggttctct gcgggtccgg gagcacccca tcctgggccc gtacgtgcag gacctgtcca    660
aattggctgt gacctcctac gcagacattg ctgacctcat ggactgtgga aataaagcac    720
ggactgtggc tgccaccaac atgaatgaga ccagcagccg ttcccatgcc gtctttacca    780
tcgtcttcac acagcgctgc catgaccagc tcacggggct ggactcggag aaggtcagta    840
agatcagttt ggtggacctt gctgggagtg agcgagccga ctcctcaggg gcccggggca    900
tgcgcctgaa ggaaggagcc aacatcaata agtccctgac tacactaggg aaagtgatct    960
cggcccttgc agatatgcaa tcaaagaagc gaaagtcgga ttttatcccc tacagggact   1020
ctgtgctcac ctggctgctc aaggaaaatt tggggggggaa ctcacgcaca gccatgattg   1080
cagccctgag ccctgctgac atcaattacg aggagactct cagcaccctc aggtatgctg   1140
accgcaccaa gcaaatccgc tgcaatgcca tcatcaacga ggaccctaat gcccggctga   1200
ttagagagct gcaggaggaa gtagcccggc tgcgggaact gctgatggct cagggactgt   1260
cagcctctgc tctggaaggc ctgaagacgg aagaagggag tgtcagaggc gccctgccag   1320
ctgtgtcatc tcccccagct ccagtttcac cctcatcacc caccacacat aatggggagc   1380
tggagccgtc attctccccc aacacggagt cccagattgg gcctgaggaa gccatggaga   1440
ggctgcagga gacagagaag attatagctg agctgaacga gacatgggag gagaagctac   1500
gcaagacaga agccctgagg atggagagag aagcattgct ggctgagatg ggggtggccg   1560
tccgggagga tgggggaact gtgggcgtct tctctccaaa gaagactccc cacctggtga   1620
acctgaacga agaccctctg atgtctgagt gtctgctcta ccacatcaaa gatggcgtca   1680
ccagggtcgg ccaagtagat atggacatca agctgaccgg acagttcatt cgggagcaac   1740
actgtctgtt ccggagcatc ccccagccag atggagaagt ggtggtcact ctggagcctt   1800
gtgaaggagc tgagacatat gtgaatggga agcttgtgac ggagccgctg gtgctgaagt   1860
cagggaatag gattgtgatg ggcaagaacc acgttttccg cttcaaccac ccggagcagg   1920
caaggctgga acgggaacga ggggtccccc cacccccagg accgccctct gagccagtcg   1980
actggaactt tgcccagaag gaactgctgg agcagcaagg catcgacata aagctggaaa   2040
tggagaagag gctgcaggat ctggagaatc agtaccggaa agaaaaggaa gaagccgatc   2100
ttctgctgga gcagcagcag ctgtatgcag actcggacag cggggatgac tctgacaagc   2160
gctcttgtga agagagctgg aggctcatct cctccttgcg ggagcagctg ccgcccacca   2220
cggtccagac cattgtcaaa cgctgtggtc tgcccagcag tggcaagcgc agggcccctc   2280
gcagggttta tcagatcccc cagcgacgca ggctgcaggg caaagacccc cgctgggcca   2340
ccatggctga cctgaagatg caggcggtga aggagatctg ctacgaggtg gccctggctg   2400
acttccgcca cgggcgggct gagattgagg ccctggccgc cctcaagatg cgggagctgt   2460
gtcgcaccta tggcaagcca gacggccccg gagacgcctg gagggctgtg gcccgggatg   2520
tctgggacac tgtaggcgag gaggaaggag gtggagctgg cagtggtggt ggcagtgagg   2580
agggagcccg aggggcggag gtggaggacc tccgggccca catcgacaag ctgacgggga   2640
ttctgcagga ggtgaagctg cagaacagca gcaaggaccg ggagctgcag gccctgcggg   2700
accgcatgct ccgcatggag agggtcatcc ccctggccca ggatcatgag gatgagaatg   2760
```

aagaaggtgg tgaggtcccc tgggccccgc ctgaaggatc agaggcagca gaggaggcag 2820
cccccagtga ccgcatgccg tcagcccggc ccccctcgcc accactgtca agctgggagc 2880
gggtgtcacg gctcatggag gaggaccctg ccttccgtcg tggtcgtctt cgctggctca 2940
agcaggagca gctacggctg cagggactgc agggtctctg ggggccgggg cggggggtgc 3000
gcaggccccc agcccgcttt gtgccccctc acgactgcaa cgtacgcttc cccttcaaga 3060
gcaaccccca gcaccgggag tcttggccag ggatggggag cggggaggct ccaactccgc 3120
tccaaccccc tgaggaggtc actccccatc cagccacccc tgcccgccgg cctccgagtc 3180
cccgaaggtc ccaccatccc cgcaggaact ccctggatgg agggggccga tcccggggag 3240
cgggttctgc acagcctgaa ccccagcact tccagcccaa aaagcacaac tcttatcccc 3300
agccacccca accctaccca gcccagcggc ccccagggcc ccgctacccc ccatacacta 3360
ctcccccacg aatgagacgg cagcgttctg cccctgacct caaggagagt ggggcagctg 3420
tgtgagtccc acatcctggg cagagggcct ggtggggccc cttgctagga gaagggaaga 3480
cgcccgagac gctgcttccc cagaagtgct ggggcaggga ggccaggaga tgagagagaa 3540
ggtcgagtag gtgatagaag acaaggggga gaccgagccg gcatggagga aaggaagagg 3600
gcacggagtt gccaaggagc aaaccaaagt gaagagagag ataggaagct gcctcggggc 3660 cacccccttgc aaaagggggt gtgtcccaca aacgctgcta tgggaggggt ggggggctgg 3720
ggtgctgcgt acgcagtgtt tgactttctt ttcaagtggg ggaaagtggg agaggactga 3780
gagtgaggca agttctcccc agccccagcc ctgtccgtct gtctgtctgt ctgtggtggt 3840
ttctgtttct tgggaggcta ggtaggatca taagtcattc ccctcccctt ccaggcctcc 3900
tgctatattt gggggactga ctggtttggc tgggagtcca tgaggatgtg ggcctttaat 3960
aaaggatagc aaacaggaaa aaaaaaaaaa aaaaaaaaaa aaaaaaaaaa aaaaaaaaaa 4020
aaaaaaaaaa aaaaaaaaaa aaaaaaaaaa aaaaaaagaa aaaaaaaaaa aaaaaaaaaa 4080
aa 4082

<210> SEQ ID NO 10
<211> LENGTH: 334
<212> TYPE: DNA
<213> ORGANISM: Artificial sequence
<220> FEATURE:
<223> OTHER INFORMATION: PCR product of KIF1C FHA domain

<400> SEQUENCE: 10
aaaaaaccat gggcactccc cacctggtga acctgaacga agaccctctg atgtctgagt 60
gtctgctcta ccacatcaaa gatggcgtca ccagggtcgg ccaagtagat atggacatca 120
agctgaccgg acagttcatt cgggagcaac actgtctgtt ccggagcatc ccccagccag 180
atggagaagt ggtggtcact ctggagcctt gtgaaggagc tgagacatat gtgaatggga 240
agcttgtgac ggagccgctg gtgctgaagt cagggaatag gattgtgatg ggcaagaacc 300
acgttttccg cttcaaccac gcggccgcaa aaaa 334

<210> SEQ ID NO 11
<211> LENGTH: 1103
<212> TYPE: PRT
<213> ORGANISM: Homo sapiens

<400> SEQUENCE: 11

Met Ala Gly Ala Ser Val Lys Val Ala Val Arg Val Arg Pro Phe Asn
1 5 10 15

-continued

```
Ala Arg Glu Thr Ser Gln Asp Ala Lys Cys Val Val Ser Met Gln Gly
            20                  25                  30

Asn Thr Thr Ser Ile Ile Asn Pro Lys Gln Ser Lys Asp Ala Pro Lys
        35                  40                  45

Ser Phe Thr Phe Asp Tyr Ser Tyr Trp Ser His Thr Ser Thr Glu Asp
    50                  55                  60

Pro Gln Phe Ala Ser Gln Gln Gln Val Tyr Arg Asp Ile Gly Glu Glu
65                  70                  75                  80

Met Leu Leu His Ala Phe Glu Gly Tyr Asn Val Cys Ile Phe Ala Tyr
                85                  90                  95

Gly Gln Thr Gly Ala Gly Lys Ser Tyr Thr Met Met Gly Arg Gln Glu
            100                 105                 110

Pro Gly Gln Gln Gly Ile Val Pro Gln Leu Cys Glu Asp Leu Phe Ser
        115                 120                 125

Arg Val Ser Glu Asn Gln Ser Ala Gln Leu Ser Tyr Ser Val Glu Val
    130                 135                 140

Ser Tyr Met Glu Ile Tyr Cys Glu Arg Val Arg Asp Leu Leu Asn Pro
145                 150                 155                 160

Lys Ser Arg Gly Ser Leu Arg Val Arg Glu His Pro Ile Leu Gly Pro
                165                 170                 175

Tyr Val Gln Asp Leu Ser Lys Leu Ala Val Thr Ser Tyr Ala Asp Ile
            180                 185                 190

Ala Asp Leu Met Asp Cys Gly Asn Lys Ala Arg Thr Val Ala Ala Thr
        195                 200                 205

Asn Met Asn Glu Thr Ser Ser Arg Ser His Ala Val Phe Thr Ile Val
    210                 215                 220

Phe Thr Gln Arg Cys His Asp Gln Leu Thr Gly Leu Asp Ser Glu Lys
225                 230                 235                 240

Val Ser Lys Ile Ser Leu Val Asp Leu Ala Gly Ser Glu Arg Ala Asp
                245                 250                 255

Ser Ser Gly Ala Arg Gly Met Arg Leu Lys Glu Gly Ala Asn Ile Asn
            260                 265                 270

Lys Ser Leu Thr Thr Leu Gly Lys Val Ile Ser Ala Leu Ala Asp Met
        275                 280                 285

Gln Ser Lys Lys Arg Lys Ser Asp Phe Ile Pro Tyr Arg Asp Ser Val
    290                 295                 300

Leu Thr Trp Leu Leu Lys Glu Asn Leu Gly Gly Asn Ser Arg Thr Ala
305                 310                 315                 320

Met Ile Ala Ala Leu Ser Pro Ala Asp Ile Asn Tyr Glu Glu Thr Leu
                325                 330                 335

Ser Thr Leu Arg Tyr Ala Asp Arg Thr Lys Gln Ile Arg Cys Asn Ala
            340                 345                 350

Ile Ile Asn Glu Asp Pro Asn Ala Arg Leu Ile Arg Glu Leu Gln Glu
        355                 360                 365

Glu Val Ala Arg Leu Arg Glu Leu Leu Met Ala Gln Gly Leu Ser Ala
    370                 375                 380

Ser Ala Leu Glu Gly Leu Lys Thr Glu Glu Gly Ser Val Arg Gly Ala
385                 390                 395                 400

Leu Pro Ala Val Ser Ser Pro Pro Ala Pro Val Ser Pro Ser Ser Pro
                405                 410                 415

Thr Thr His Asn Gly Glu Leu Glu Pro Ser Phe Ser Pro Asn Thr Glu
            420                 425                 430
```

-continued

```
Ser Gln Ile Gly Pro Glu Glu Ala Met Glu Arg Leu Gln Glu Thr Glu
        435                 440                 445

Lys Ile Ile Ala Glu Leu Asn Glu Thr Trp Glu Glu Lys Leu Arg Lys
    450                 455                 460

Thr Glu Ala Leu Arg Met Glu Arg Glu Ala Leu Leu Ala Glu Met Gly
465                 470                 475                 480

Val Ala Val Arg Glu Asp Gly Gly Thr Val Gly Val Phe Ser Pro Lys
                485                 490                 495

Lys Thr Pro His Leu Val Asn Leu Asn Glu Asp Pro Leu Met Ser Glu
            500                 505                 510

Cys Leu Leu Tyr His Ile Lys Asp Gly Val Thr Arg Val Gly Gln Val
        515                 520                 525

Asp Met Asp Ile Lys Leu Thr Gly Gln Phe Ile Arg Glu Gln His Cys
    530                 535                 540

Leu Phe Arg Ser Ile Pro Gln Pro Asp Gly Glu Val Val Val Thr Leu
545                 550                 555                 560

Glu Pro Cys Glu Gly Ala Glu Thr Tyr Val Asn Gly Lys Leu Val Thr
                565                 570                 575

Glu Pro Leu Val Leu Lys Ser Gly Asn Arg Ile Val Met Gly Lys Asn
            580                 585                 590

His Val Phe Arg Phe Asn His Pro Glu Gln Ala Arg Leu Glu Arg Glu
        595                 600                 605

Arg Gly Val Pro Pro Pro Pro Gly Pro Pro Ser Glu Pro Val Asp Trp
    610                 615                 620

Asn Phe Ala Gln Lys Glu Leu Leu Glu Gln Gln Gly Ile Asp Ile Lys
625                 630                 635                 640

Leu Glu Met Glu Lys Arg Leu Gln Asp Leu Glu Asn Gln Tyr Arg Lys
                645                 650                 655

Glu Lys Glu Glu Ala Asp Leu Leu Leu Glu Gln Gln Gln Leu Tyr Ala
            660                 665                 670

Asp Ser Asp Ser Gly Asp Asp Ser Asp Lys Arg Ser Cys Glu Glu Ser
        675                 680                 685

Trp Arg Leu Ile Ser Ser Leu Arg Glu Gln Leu Pro Pro Thr Thr Val
    690                 695                 700

Gln Thr Ile Val Lys Arg Cys Gly Leu Pro Ser Ser Gly Lys Arg Arg
705                 710                 715                 720

Ala Pro Arg Arg Val Tyr Gln Ile Pro Gln Arg Arg Arg Leu Gln Gly
                725                 730                 735

Lys Asp Pro Arg Trp Ala Thr Met Ala Asp Leu Lys Met Gln Ala Val
            740                 745                 750

Lys Glu Ile Cys Tyr Glu Val Ala Leu Ala Asp Phe Arg His Gly Arg
        755                 760                 765

Ala Glu Ile Glu Ala Leu Ala Ala Leu Lys Met Arg Glu Leu Cys Arg
    770                 775                 780

Thr Tyr Gly Lys Pro Asp Gly Pro Gly Asp Ala Trp Arg Ala Val Ala
785                 790                 795                 800

Arg Asp Val Trp Asp Thr Val Gly Glu Glu Glu Gly Gly Gly Ala Gly
                805                 810                 815

Ser Gly Gly Gly Ser Glu Glu Gly Ala Arg Gly Ala Glu Val Glu Asp
            820                 825                 830

Leu Arg Ala His Ile Asp Lys Leu Thr Gly Ile Leu Gln Glu Val Lys
        835                 840                 845

Leu Gln Asn Ser Ser Lys Asp Arg Glu Leu Gln Ala Leu Arg Asp Arg
```

-continued

```
    850                 855                 860

Met Leu Arg Met Glu Arg Val Ile Pro Leu Ala Gln Asp His Glu Asp
865                 870                 875                 880

Glu Asn Glu Glu Gly Gly Glu Val Pro Trp Ala Pro Pro Glu Gly Ser
                885                 890                 895

Glu Ala Ala Glu Glu Ala Ala Pro Ser Asp Arg Met Pro Ser Ala Arg
            900                 905                 910

Pro Pro Ser Pro Pro Leu Ser Ser Trp Glu Arg Val Ser Arg Leu Met
        915                 920                 925

Glu Glu Asp Pro Ala Phe Arg Arg Gly Arg Leu Arg Trp Leu Lys Gln
    930                 935                 940

Glu Gln Leu Arg Leu Gln Gly Leu Gln Gly Leu Trp Gly Pro Gly Arg
945                 950                 955                 960

Gly Val Arg Arg Pro Pro Ala Arg Phe Val Pro Pro His Asp Cys Asn
                965                 970                 975

Val Arg Phe Pro Phe Lys Ser Asn Pro Gln His Arg Glu Ser Trp Pro
            980                 985                 990

Gly Met Gly Ser Gly Glu Ala Pro  Thr Pro Leu Gln Pro  Pro Glu Glu
        995                 1000                1005

Val Thr  Pro His Pro Ala Thr  Pro Ala Arg Arg Pro  Pro Ser Pro
    1010                 1015                 1020

Arg Arg  Ser His His Pro Arg  Arg Asn Ser Leu Asp  Gly Gly Gly
    1025                 1030                 1035

Arg Ser  Arg Gly Ala Gly Ser  Ala Gln Pro Glu Pro  Gln His Phe
    1040                 1045                 1050

Gln Pro  Lys Lys His Asn Ser  Tyr Pro Gln Pro Pro  Gln Pro Tyr
    1055                 1060                 1065

Pro Ala  Gln Arg Pro Pro Gly  Pro Arg Tyr Pro Pro  Tyr Thr Thr
    1070                 1075                 1080

Pro Pro  Arg Met Arg Arg Gln  Arg Ser Ala Pro Asp  Leu Lys Glu
    1085                 1090                 1095

Ser Gly  Ala Ala Val
    1100
```